(12) United States Patent
Chalubert et al.

(10) Patent No.: US 8,155,787 B2
(45) Date of Patent: Apr. 10, 2012

(54) INTELLIGENT INTERFACE DEVICE FOR GRASPING OF AN OBJECT BY A MANIPULATING ROBOT AND METHOD OF IMPLEMENTING THIS DEVICE

(75) Inventors: Gerard Chalubert, Voisins le Bretonneux (FR); Christophe Leroux, Versailles (FR)

(73) Assignee: Commissariat a l'Energie Atomique, Paris (FR)

( * ) Notice: Subject to any disclaimer, the term of this patent is extended or adjusted under 35 U.S.C. 154(b) by 700 days.

(21) Appl. No.: 12/294,892

(22) PCT Filed: Mar. 23, 2007

(86) PCT No.: PCT/EP2007/052816
§ 371 (c)(1),
(2), (4) Date: Sep. 26, 2008

(87) PCT Pub. No.: WO2007/110391
PCT Pub. Date: Oct. 4, 2007

(65) Prior Publication Data
US 2010/0172733 A1  Jul. 8, 2010

(30) Foreign Application Priority Data
Mar. 27, 2006  (FR) ...................................... 06 51045

(51) Int. Cl.
*G05B 11/00* (2006.01)

(52) U.S. Cl. .......................................... 700/245; 901/1

(58) Field of Classification Search .......... 700/245–249, 700/258–259; 318/568.11, 568.12, 568.16, 318/568.21; 901/1–2, 9; 414/1–2
See application file for complete search history.

(56) References Cited

U.S. PATENT DOCUMENTS

| | | | |
|---|---|---|---|
| 6,218,802 B1 | 4/2001 | Onoue et al. | |
| 7,210,890 B2 * | 5/2007 | Curotto et al. | 414/408 |
| 7,561,141 B2 * | 7/2009 | Shahoian et al. | 345/156 |

FOREIGN PATENT DOCUMENTS

| | | |
|---|---|---|
| JP | 04229167 | 8/1992 |
| JP | 07040273 | 2/1995 |
| WO | 0184260 A2 | 11/2001 |

OTHER PUBLICATIONS

French Preliminary International Search Report of PCT/EP2007/052816, dated Jun. 10, 2008.

Bley, Florian et al., "Supervised Navigation and Manipulation for Impaired Wheelchair Users," 2004 IEEE International Conference on Systems, Man and Cybernetics, 2004, pp. 2790-2796.

* cited by examiner

*Primary Examiner* — Dalena Tran
(74) *Attorney, Agent, or Firm* — Nixon Peabody LLP

(57) ABSTRACT

An intelligent interface device for grasping an object includes a manipulating robot comprising a hinged arm provided with a clamp at its free end and equipped with at least one camera, a computer with a display screen and an input unit, means for controlling the clamp, means for displaying the video image of the object taken by a camera on the display screen, means for graphically identifying a selection area surrounding the object in this image using the input unit.

13 Claims, 3 Drawing Sheets

_US 8,155,787 B2_

INTELLIGENT INTERFACE DEVICE FOR GRASPING OF AN OBJECT BY A MANIPULATING ROBOT AND METHOD OF IMPLEMENTING THIS DEVICE

CROSS REFERENCE TO RELATED APPLICATIONS OR PRIORITY CLAIM

This application is a national phase of International Application No. PCT/EP2007/052816, entitled "INTELLIGENT INTERFACE DEVICE FOR INPUTTING AN OBJECT BY A MANIPULATING ROBOT AND METHOD OF IMPLEMENTING THIS DEVICE", which was filed on Mar. 23, 2007, and which claims priority of French Patent Application No. 06 51045, filed Mar. 27, 2006.

DESCRIPTION

1. Technical Field

The present invention concerns an intelligent interface device for grasping of an object by a manipulating robot and a method of implementing this device.

The field of the invention is that of assistance for physically dependent persons, in particular handicapped persons. The field of the invention is also that of assistance for manipulating objects in hostile environments to lighten the task of the operator, for example in an underwater or nuclear environment, with potential force feedback.

In the continuation of the description, as an example, we will consider assistance for handicapped persons.

2. Prior Art

Despite their potential usefulness and developments made since several decades ago, robots remain infrequently used in the general public and more specifically in the field of assistance for handicapped persons, in particular due to their high cost, but also due to their complexity. This complexity makes their use difficult for people not familiar with the technology, and the smallest problem quickly becomes insurmountable.

Grasping an object via a robot, for example a manipulating arm provided with a clamp, can be broken down into two phases: approaching the object, then gripping this object using the clamp. The approach phase corresponds to movement in free space, the objective being to position the clamp geometrically in relation to the object. In the gripping phase, the problem is to ensure stable holding of the object.

In industrial robotics, it is possible to conduct grasping operations in an open loop by using the repeatability of the manipulating arm, i.e. its capacity to repeat a previously learned movement. The position and the type of the objects to be grasped or deposited is then perfectly known beforehand. When the position of the objects to grasp is not known beforehand, such an approach cannot be used. The manipulating arms traditionally having poor precision, the use of sensors, for example video cameras, to guide the movements of an arm toward an object to be grasped become a necessity.

In the case where the object to be grasped is known, it is possible to successfully conduct a grasping operation by using servoing techniques. A visual servoing consists of controlling the movements of the arm according to the gaps observed between a reference to be reached and the current information provided by a vision system. Visual servoings are usually classified into 3D (three dimensions) servoing, servoing using 3D information generally reprocessed from a model of the object observed and its image, and 2D servoings, the servoing using image information only. One can also use 2D ½ servoings, by estimating a homography in relation to a reference plane on the target, between a current image and a desired image at each iteration of the control law.

In the case where the object to be grasped is not known, one can distinguish solutions using a vision system observing the clamp and the object to be grasped, and those using a sensor mounted on the clamp of the robot. These solutions of the prior art then require marking or a geometric model of the objects to be grasped.

One document of the prior art, reference [1] at the end of the description, describes a method for grasping an object using a robot arm provided with a camera taking images of an environment of the object including the object, during the movements of the arm. This method comprises steps for localization of the object by calculating the coordinates of determined points of the object in the environment in relation to the robot arm, according to positions of said determined points in the images. As illustrated in FIG. 1, a robot arm 11 equipped with a camera 12 and ending on a clamp 13 thus makes it possible to reach and grasp an object 14 placed on a table 15. The operator has a computer 16 with a screen and keyboard to control the arm. The camera 12 takes an image of the environment located in front of it. The localization method includes the selection of a certain number of points on the image.

The aim of the invention is to improve this method of grasping an object by proposing an intelligent interface device for grasping of an object by a manipulating robot, and a method for implementation of this device which does not require marking of the object or the use of a model of the object, which is easy to implement, the activity required for use being minimized, which is versatile, can be applied to a very large variety of objects, and requires only a reduced learning time, by hiding the technology of the equipment used.

DISCLOSURE OF THE INVENTION

The invention concerns an intelligent interface device for grasping of an object comprising:
  a manipulating robot comprising a hinged arm provided with a clamp at its free end and equipped with at least one camera,
  a computer with a display screen and an input unit,
  means of controlling the clamp,
  means of displaying the video image of the object taken by a camera on the display screen,
  characterized in that it further comprises:
  means of graphically identifying a selection area surrounding the object in this image using the input unit, and
  in that the means of controlling the clamp comprise a graphic control button able to be actuated from the display screen and corresponding to at least one of the following commands:
  move the clamp to the left,
  move the clamp to the right,
  move the clamp downward,
  move the clamp upward,
  move the clamp forward,
  move the clamp backward,
  open/close the clamp,
  turn the clamp clockwise,
  turn the clamp counterclockwise,
  validate,
  cancel,
  immediate stop.

In one advantageous embodiment, this device comprises two cameras forming a stereoscopic video sensor. The input unit can in particular be a mouse, head tracking, a contactor, a virtual keyboard, a joystick, or an ocular tracking or voice synthesis system.

Each control can correspond to a "click" on an icon shown on the display screen. Advantageously, the clamp is equipped with an optical barrier.

In one embodiment, the robot is fixed to the arm of a wheelchair. In another embodiment, the robot is fixed on a mobile platform.

The device according to the invention uses equipment with a low cost and small bulk, which enables broad use. Furthermore, the time needed to learn this device is several minutes for a qualified user.

The invention also concerns a method for implementation of an intelligent interface device for grasping of an object comprising:
- a manipulating robot comprising a hinged arm provided with a clamp at its free end and equipped with at least one camera,
- a computer with a display screen and an input unit,
characterized in that it comprises the following steps:
- bring the object into the field of vision of a camera by controlling the movement of the clamp, the video image taken by the camera being displayed on the display screen,
- identify a selection area around the object using the input unit,
- discriminate between the object and its environment, and estimate the distance between the clamp and the object,
- calculate the center of gravity of the object in the image,
- calculate a set speed according to the distance to be traveled by the clamp to reach the object,
- move the clamp into the vicinity of the object,
- move the clamp blindly and close the clamp on the object,
- bring the object back toward the user.

The selection area surrounding the object can be a rectangular area, a graphical lasso defined by several points selected by the user, or the trace of a closed line surrounding the object.

In this method one can use two cameras forming a stereoscopic video sensor. One can then select points of interest in the two images coming from the two cameras, and match these points two by two. One can also correct images coming from both cameras.

EMBODIMENTS OF THE INVENTION

Figure 1:
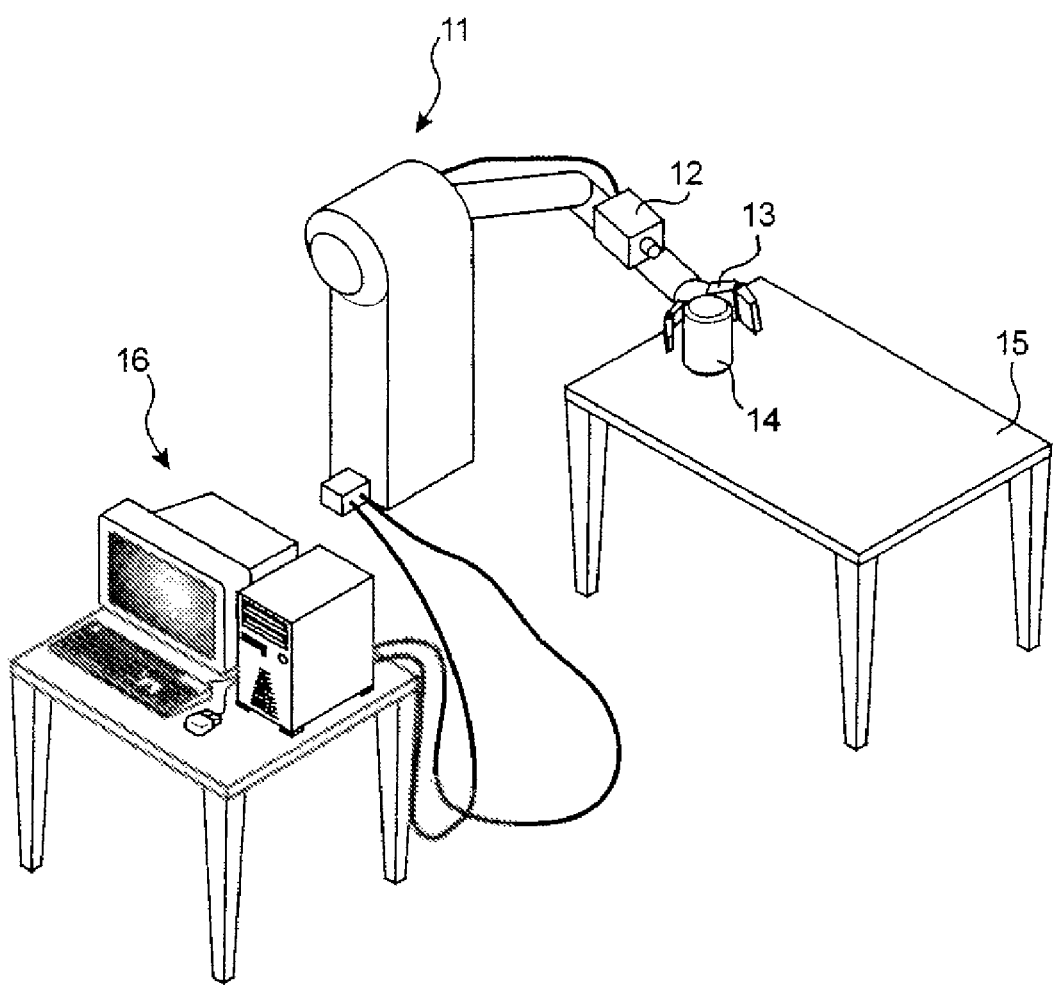
FIG. 1 illustrates a device of the prior art.
Figure 2:
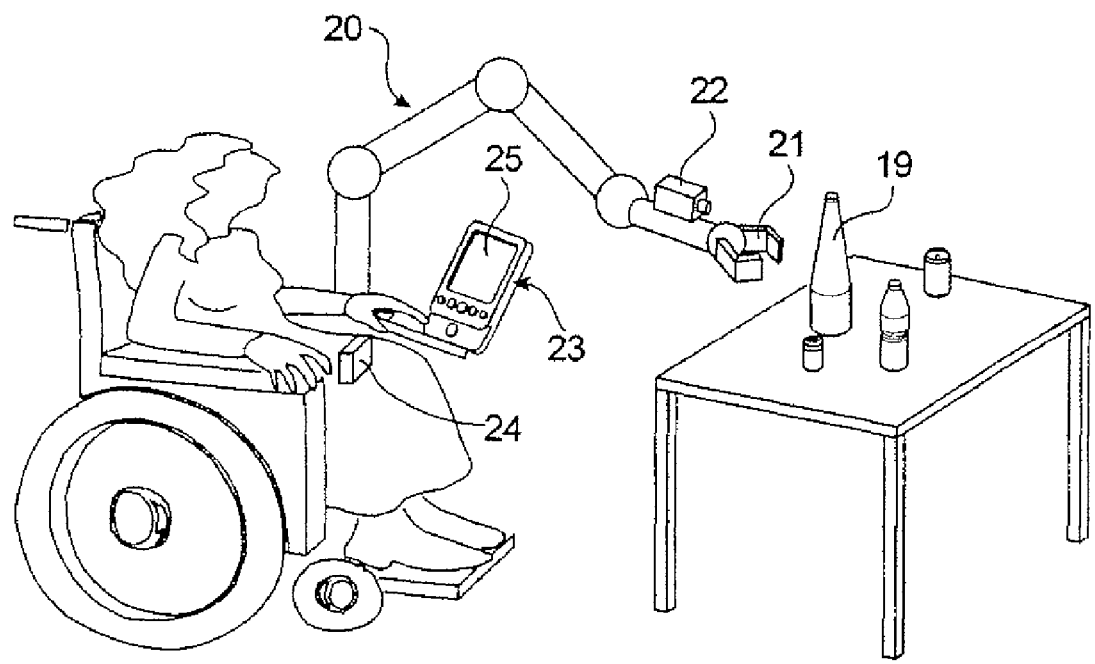
FIGS. 2 and 3 illustrate the device according to the invention.

As illustrated in FIG. 2, the intelligent interface device for grasping of an object 19 according to the invention comprises:
- a manipulating robot comprising a hinged arm 20 provided with a clamp 21 at its free end and equipped with at least one camera 22, for example two cameras forming a stereoscopic video sensor,
- a computer 23 with a display screen 25 and an input unit 24,
- means of controlling the movement and opening of the clamp 21,
- means of displaying the video image of the object taken by the camera 22 on the display screen 25.

As illustrated in FIG. 2, the arm 20 can be fixed to the arm of a wheelchair, for example of a handicapped person. But it can also be fixed on a mobile platform, the computer then being arranged on this platform, the display screen and the control unit being accessible to the person.

Figure 3:
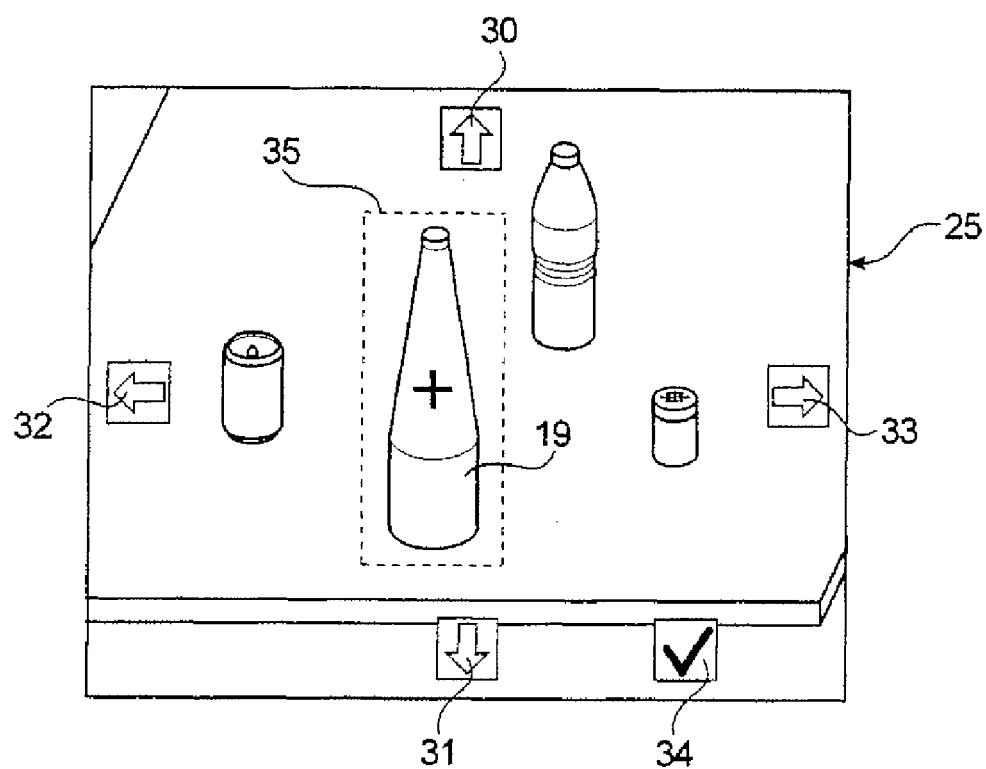

As illustrated in FIG. 3, the device according to the invention further comprises:
- means of graphically identifying a selection area 35, for example rectangular, surrounding the object 19 in this image using the input unit 24.

The means of controlling the clamp can include the following commands:
- move the clamp to the left,
- move the clamp to the right,
- move the clamp downward,
- move the clamp upward,
- move the clamp forward,
- move the clamp backward,
- open/close the clamp,
- validate the selected object and trigger automatic gripping of the object,
- cancel the selected object or stop the arm,
- immediate stop.

In the embodiment illustrated in FIG. 3, a simple "click" or a continuous "click" on a corresponding icon of the display screen makes it possible to validate one of these functions. In this embodiment, the graphic identification means are piloted by four commands 30 (upward movement), 31 (downward movement), 32 (leftward movement) and 33 (rightward movement) to trace a rectangular area 35 surrounding the object 19, and a validation command 34. The device according to the invention thus has a minimal number of commands. It is intuitive and easy to use. It completely hides the technical aspect. It is made up of a window displaying the video return from the camera, four controls allowing movement of the clamp, a validation command. It may further include a stop command to halt the movement of the arm in case of problems.

Figure 4:
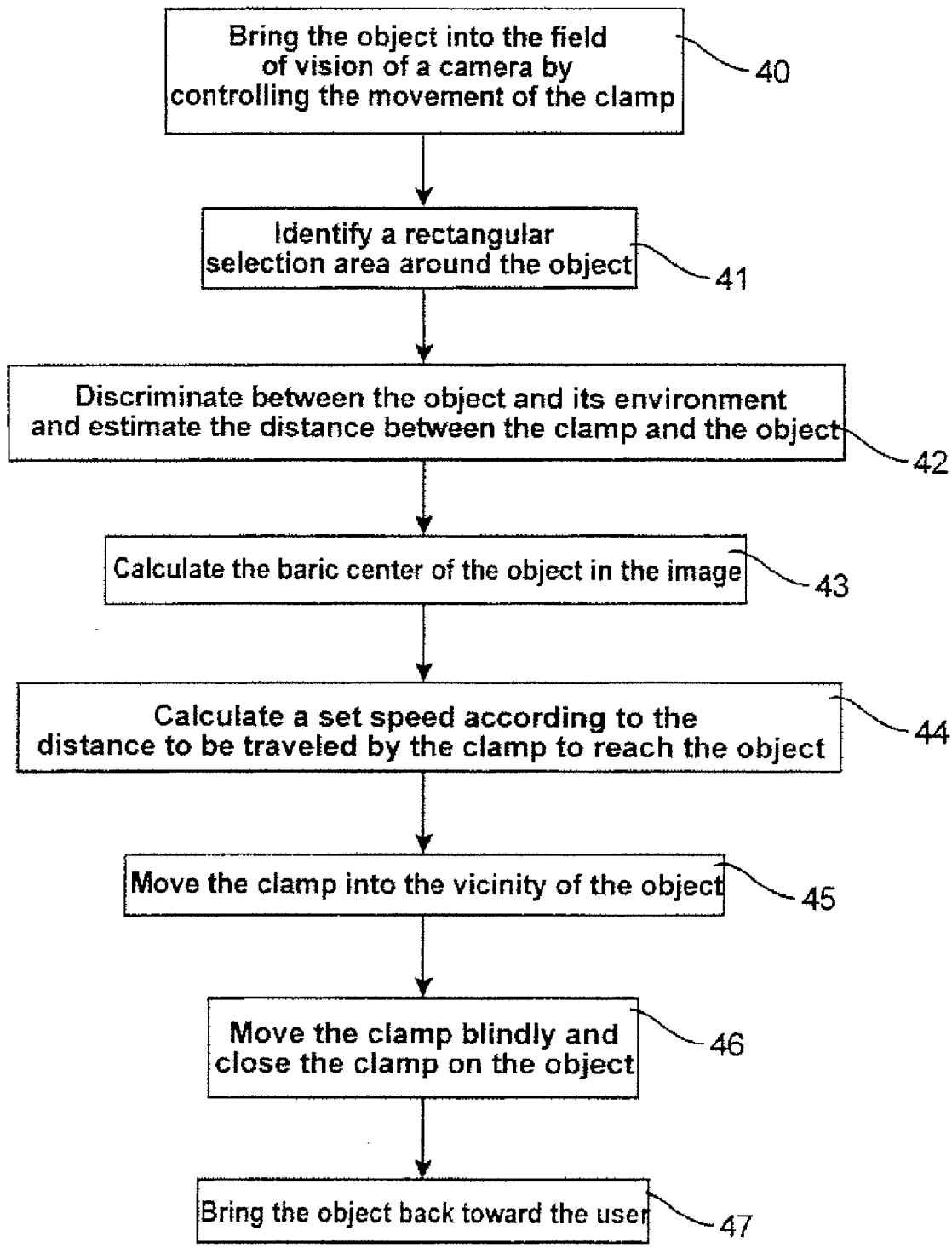
FIG. 4 illustrates the steps of the method according to the invention.

The method for implementing this device comprises the following steps, illustrated in FIG. 4:
- bring the object into the field of vision of a camera by controlling the movement of the clamp, the video image taken by this camera being displayed on the display screen (step 40),
- identify a selection area, for example rectangular, around the object using the input unit (step 41),
- discriminate between the designated object and its environment, and estimate the distance between the clamp and the object (step 42),
- calculate the center of gravity of the object in the image (step 43),
- calculate a set speed according to the distance to be traveled by the clamp in order to reach the object (step 44),
- move the clamp up to approximately ten centimeters from the object (step 45),
- move the clamp blindly and close the clamp on the object (step 46),
- bring the object back toward the user (step 47).

In one embodiment, the robot used is an ARM (MANUS) manipulating arm from the company ExactDyanmics, as described in reference document [2], controlled by a controller. The cameras are Webcams. The cameras are used both to guide the movement of the robot through visual servoing and to provide information to the user. The clamp is equipped with an optical barrier which makes it possible to precisely detect the moment when the object is grasped in the jaw of the clamp. The computer is a PC ("Personal Computer") type computer, 2.8 GHz. The computer is connected to the controller of the robot through a CAN ("Controller Area Network") bus.

The device according to the invention can interface with all available input units: mouse, head tracking, contactor, virtual keyboard, armchair joystick, ocular monitoring system, voice synthesis system, etc.

In one embodiment using a stereoscopic video sensor with two cameras whereof the focal axes are parallel, during steps 41 and following, once the selection area is defined around the object in the image, one localizes and identifies the object designated by the user. This localization is based on the hypothesis that the determined object, which is displayed, is dominant in relation to the other objects and in relation to the background of the scene.

One can then automatically select points of interest in the two images resulting from the two cameras. The technique used to connect these points is a voting technique consisting of choosing the group of points whereof the distance to the camera is the most frequent.

The points extracted in both images are connected based on an epipolar geometry in which one uses the knowledge of the transformation which took place between the two images. For example in the case of a translational movement to the right, one expects that the points move on horizontal lines. Likewise, in the case of translational movement toward the object, one expects that the points will move away from the center of the zoom along lines going out from this center. This is what is referred to as respect of the epipolar constraint.

Each pairing contributes to a distance hypothesis. Once all pairing hypotheses are done, the selection of the object consists of choosing the most frequent distance. One then assumes that this distance corresponds to the designated object. One then uses the center of gravity of the connected points to localize the direction in which the object is found. Once this localization is done, the process is repeated during the movements of the robot to ensure a correct approach toward the object.

One can further use the internal and external parameters of the two cameras to improve the results. This is what is called image correction. One then corrects the distortion effects and straightens out the epipolar geometry so that the epipolar lines are horizontal lines.

As a safety measure, the movement of the robot can, at any time, be interrupted by the user by actuating an "immediate stop" button displayed on the user interface.

According to one variation of the invention, the device comprises only one camera, and one takes at least two staggered images to obtain stereoscopic images of the object. The continuation of the method is identical to the case where the device comprises a stereoscopic video sensor with two cameras.

According to one variation of the invention, the selection of the area of interest around the object is not necessarily a rectangular area, but can equivalently be done in the shape of a graphical lasso defined by several points selected by the user, or by tracing a closed line surrounding the object.

According to another variation, the speed of movement of the arm can be calculated in a manner other than proportionally to the distance between the object and the clamp of the robot: for example the speed can be programmed to follow a continuous acceleration deceleration curve, with a minimum speed and a maximum speed, in order to avoid abrupt movements of the robot arm.

According to another variation of the invention, the movement of the robot arm can be servoed not in speed but in position: the estimate of the distance separating the object from the robot arm provides the orientation and the distance to be traveled by the robot arm, for example at a constant speed.

According to another variation of the invention, the interface can include additional commands for angular orientation of the clamp (for example orientation command in the clockwise direction, and counterclockwise orientation).

According to one variation of the invention, an optional additional step may consist, after selecting the points of the image, of evaluating the shape of the object, then orienting the clamp on the smallest width of the object, in order to grasp it stably.

According to another variation of the invention, the method may comprise an additional validation step, before the clamp grasps the object, so that the user confirms his or her desire to grasp the object using the clamp of the robot arm.

The invention can easily be adapted to applications other than grasping of objects by a robot arm to move this object and bring it back toward the user. In the field of remote manipulation of robots (for example underwater), the invention can allow a remote operator to draw a robot alongside a handle by approaching the end of the robot arm equipped with a stereoscopic vision system whereof the images are transmitted to a graphic user interface, then aligning it on the handle to be grasped.

In the field of remote manipulation in hostile environments, for example in the nuclear field, an operator generally must accompany all of the movements of a slave arm through the holding of a master arm. The invention can make it possible, after recognition and designation of an object to be grasped on the screen, to let the robotic arm perform all of the movements alone until the end of a predefined movement.

The invention claimed is:

1. An intelligent interface device for grasping of an object comprising:
    a manipulating robot comprising a hinged arm provided with a clamp at its free end and equipped with at least one camera,
    a computer with a display screen and an input unit,
    means for controlling the clamp,
    means for displaying a video image of the object taken by a camera on the display screen,
    characterized in that it also includes:
    means for graphically identifying a selection area surrounding the object in this image using the input unit, the means for graphically identifying being piloted by four commands for upward, downward, leftward and rightward movement to trace this selection area surrounding the object, and a validation command, and
    in that the means for controlling the clamp comprises at least one graphic control button able to be actuated from the display screen and responding to at least one of the following commands:
    move the clamp to the left,
    move the clamp to the right,
    move the clamp downward,
    move the clamp upward
    move the clamp forward,
    move the clamp backward,
    open/close the clamp,
    turn the clamp clockwise,
    turn the clamp counterclockwise,
    validate,
    cancel,
    immediate stop.

2. The device according to claim 1, comprising two cameras forming a stereoscopic video sensor.

3. The device according to claim 1, in which the input unit is a mouse, a head tracking, a contactor, a virtual keyboard, a joystick, or an ocular monitoring or voice synthesis system.

4. The device according to claim 1, in which each command corresponds to a click on an icon shown on the display screen.

5. The device according to claim 1, in which the clamp is equipped with an optical barrier, or a proximity detector.

6. The device according to claim 1, in which the robot is fixed to the arm of a wheelchair.

7. The device according to claim 1, in which the robot is fixed on a mobile platform.

8. A method for implementing an intelligent interface device for grasping of an object comprising:
   a manipulating robot comprising a hinged arm provided with a clamp at its free end and equipped with at least one camera for taking a video image,
   a computer with a display screen and an input unit,
   characterized in that it comprises the following steps:
   bring the object into the field of vision of a camera by controlling the movement of the clamp, the video image taken by the camera being displayed on the display screen,
   identify a selection area around the object using the input unit,
   discriminate between the object and its environment, and estimate a distance between the clamp and the object,
   calculate the center of gravity of the object in the image,
   calculate a set speed according to the distance to be travelled by the clamp to reach the object,
   move the clamp up to the vicinity of the object,
   move the clamp blindly and close the clamp,
   bring the object back toward the user.

9. The method according to claim 8, in which the selection area surrounding the object is a rectangular area, a graphical lasso defined by several points chosen by the user, or a closed line traced surrounding the object.

10. The method according to claim 8, in which one uses two cameras forming a stereoscopic video sensor.

11. The method according to claim 10, in which one selects points of interest in the two images coming from the two cameras.

12. The method according to claim 11, in which one pairs these points two by two.

13. The method according to claim 10, in which one corrects the images coming from the two cameras.

* * * * *